(12) United States Patent
Rathi

(10) Patent No.: US 12,402,811 B2
(45) Date of Patent: Sep. 2, 2025

(54) NEUROMUSCULAR TESTING DEVICE AND METHOD TO USE

(71) Applicant: Prachi Rathi, Jacksonville, FL (US)

(72) Inventor: Prachi Rathi, Jacksonville, FL (US)

( * ) Notice: Subject to any disclaimer, the term of this patent is extended or adjusted under 35 U.S.C. 154(b) by 955 days.

(21) Appl. No.: 17/520,179

(22) Filed: Nov. 5, 2021

(65) Prior Publication Data
US 2023/0141165 A1    May 11, 2023

(51) Int. Cl.
| | | |
|---|---|---|
| *A61B 5/103* | (2006.01) | |
| *A61B 5/00* | (2006.01) | |
| *A61B 5/107* | (2006.01) | |
| *A61B 5/11* | (2006.01) | |
| *A61B 90/92* | (2016.01) | |
| *A61B 90/00* | (2016.01) | |

(52) U.S. Cl.
CPC .......... *A61B 5/1121* (2013.01); *A61B 5/1071* (2013.01); *A61B 5/7405* (2013.01); *A61B 90/92* (2016.02); *A61B 2090/067* (2016.02)

(58) Field of Classification Search
CPC ..... A61B 5/1121; A61B 90/92; A61B 5/1071; A61B 5/7405; A61B 2090/067; A61B 5/4064; A61B 5/4082; A61B 5/1124; A61H 1/0274; A61H 1/0285; A61H 2201/5069; G09B 19/003
See application file for complete search history.

(56) References Cited

U.S. PATENT DOCUMENTS

| | | | |
|---|---|---|---|
| 8,758,277 B2 | 6/2014 | Rathi | |
| 2007/0266579 A1* | 11/2007 | Briscoe | ................ A61B 5/1071 33/503 |
| 2009/0299233 A1* | 12/2009 | Wang | .................. A61B 5/4023 600/595 |

* cited by examiner

*Primary Examiner* — Etsub D Berhanu
*Assistant Examiner* — Lucy Eppert
(74) *Attorney, Agent, or Firm* — Lawrence J. Gibney

(57) ABSTRACT

Health care professionals must often measure a person's neuromuscular function. Currently there is no way to accurately assess the level of a person's ability to perform basic tasks that will permit the person to perform the activities of daily activity and thus determine whether the person can be discharged from the hospital or can safely transition to a different environment or whether additional assistance may be needed. This device will allow the health care professional to accurately assess these functions so that decisions regarding discharge from a health care facility or return to home may be made.

4 Claims, 10 Drawing Sheets

NEUROMUSCULAR TESTING DEVICE AND METHOD TO USE

A. FIELD OF THE INVENTION

This relates to the field of rehabilitation and specifically, a way to measure the neuromuscular function of a patient with the use of one device. Neuromuscular damage can occur as a result of stroke, head injury, or any other diseases or conditions that affect the brain or muscles.

Neuromuscular functioning controls our ability to speak, touch, feel, see, and hear in addition to allowing us to balance and walk. Individuals who have suffered any type of brain trauma or physical disability from whatever cause are likely to suffer some damage to their neuromuscular functioning.

The ability to specifically quantify during assessment and later the progress of a patient will impact decisions on whether the patient is able to be discharged alone or whether the person should have some assistance when the person returns to his or her home. In some cases, this type of measurement may also determine whether or not the person should be sent to a separate rehabilitation facility for additional therapy and services.

B. PRIOR ART

The applicant has received a patent for this type of device and that prior art reference can be found at Rathi U.S. Pat. No. 8,758,277. The current application adds a horizontal arm to measure the person's ability to reach in front of the person and to the side of the person. The horizontal arm will rotate to allow the medical care professional to measure the person's ability to use his or her wrist in rotation and flexion positions.

BRIEF SUMMARY OF THE INVENTION

One of the challenges for therapists is to be able to quantify the patient's abilities during an initial assessment and during time to measure subsequent improvement in the patient from an objective standard. This device will allow a therapist to measure both linear and angular measurements so that an objective measurement of the patient's progress can be recorded.

This is a device that is designed to be portable and can be moved with one hand. A pole will rest on a base with a protractor onto which a plurality of wheels are placed so that the entire device can be moved easily. The wheels will be lockable so that the device can be placed in one position, when needed.

The center pole can telescope so that the device can be placed at the ideal height for the individual. Ideally the nut which affixes the arms to the pole will be aligned with the person's sternum if the person is facing the device and at the acroniom process of the person if the device is sideways with respect to the patient.

This device will be helpful to measure a multitude of ranges of motions for the body parts including the shoulder, back, neck arms and wrists. It will allow the therapist to measure functional shoulder flexion, trunk flexion, trunk flexion with rotation, wrist flexion and wrist rotation and abduction and adduction of a person's limbs in addition to other body movements.

On the top of the pole will be a plurality of vertical arms that rotate around a pin that is specifically designed to be moved by a single person and called a tripod nut. On each of the vertical arms will be a series of markings that will measure the distance from a given point so that the therapist can measure the distance that the patient can move an object or touch an object. The vertical arms can be locked in place and are color coded.

Near the center of the device a horizontal arm will be secured to the pole. The horizontal arm can be moved up and down to accommodate for the height of the person. The horizontal arm can rotate along the horizontal axis to enable the therapist to measure a person's ability to reach out and/or to the side of the body. A plurality of openings on the end of the arm will allow the therapist to lock the horizontal arm in place for testing purposes; a pin is contemplated to lock the arm in place. The horizontal arm will have markings to objectively quantify a person's progress. A protractor on the end of the horizontal arm enables the therapist to measure a person's ability to use his or her wrist. For purposes of this application only one horizontal arm is depicted; the user can place more than one horizontal arm on the device.

Because some individuals may have other physical impairments including impaired vision or hearing, the arms may also be illuminated or be equipped with an audible signal.

On each vertical arm will be a window that will allow the therapist to read the degrees that are marked on the protractor that is attached to the pole. On the central end of each vertical arm will be a cutout portion or window so that the therapist can easily view the protractor that is located behind the vertical arm. This will permit the therapist to specifically measure the angle of the vertical arm so that a precise measurement can be obtained.

It is contemplated that there will be eight vertical arms used on this device and each of the vertical arms will operate independently of each other and all can lock in place.

The vertical arms and the horizontal arm are of sufficient length so that the device will test the reach of the individual including a person's diagonal reach. Because of the gradations on each of the vertical and horizontal arms, the therapist will be able to specifically determine the "amount of reach" of the person. Each therapist who interacts with the person can then easily perform follow up exercises and measurements.

The vertical arms will be on both sides of the device and the vertical arms will rotate around the pin. The system is fastened with a tripod nut.

Before a patient should be discharged from a facility such as a hospital or nursing facility, a range of the ability of the person must be carefully measured in order to insure that the transition to another environment (such as the person's home) is beneficial for the patient as well as safe for the patient.

Some of the skills that are addressed include eye movement exercise and rehabilitation for vertigo and vestibular system analysis, neck movements, eye-hand coordination, gross and fine motor coordination, visual-motor skills retraining, visual-perceptual skills, dexterity skills retraining, and cognitive skills retraining are just some of the areas that should be tested. These are a representative listing of functions to be tested and are not an exhaustive list.

On the sides of the pole will be a plurality of baskets that can telescope outward so that the person's ability to reach below the waist is tested. The baskets will be attached to the pole with a bushing that can be locked in place. Again, all the features of this device are carefully designed to test the various areas that need to be evaluated for a person's safe transition to another environment.

Another skill that is critical is the ability to reach at an angle. This simulates a person who needs to reach at an angle to place something in a cabinet or the refrigerator. With this device the person typically stands in front of the device and the therapist asks the patient to perform certain tasks. The therapist will also ask the person to perform certain maneuvers from side to side at different angles both with the vertical arms and the horizontal arm.

To measure the ability of a person to move from side to side a base protractor is affixed to the base. A pointer is also placed on the top surface of the base protractor. The pointer allows the device to be moved at an angle relative to the person to measure the ability to reach at an angle. With the protractor the therapist can make detailed, specific measurements as to the person's ability to reach from side to side.

Similarly a protractor is placed on the end of the horizontal arm to measure the person's ability to use his or her wrist. On the flange near the end of the horizontal arm are a plurality of openings to lock the horizontal arm in place along the horizontal axis during testing.

The device also has the ability to expand and incorporate other games and activities to test specific functions as the therapist modifies the activity.

BRIEF DESCRIPTION OF THE DRAWINGS

FIG. 2A is an exploded view of the stand depicting the base protractor and pointer.

NUMBERING DESCRIPTION

Figure 1:
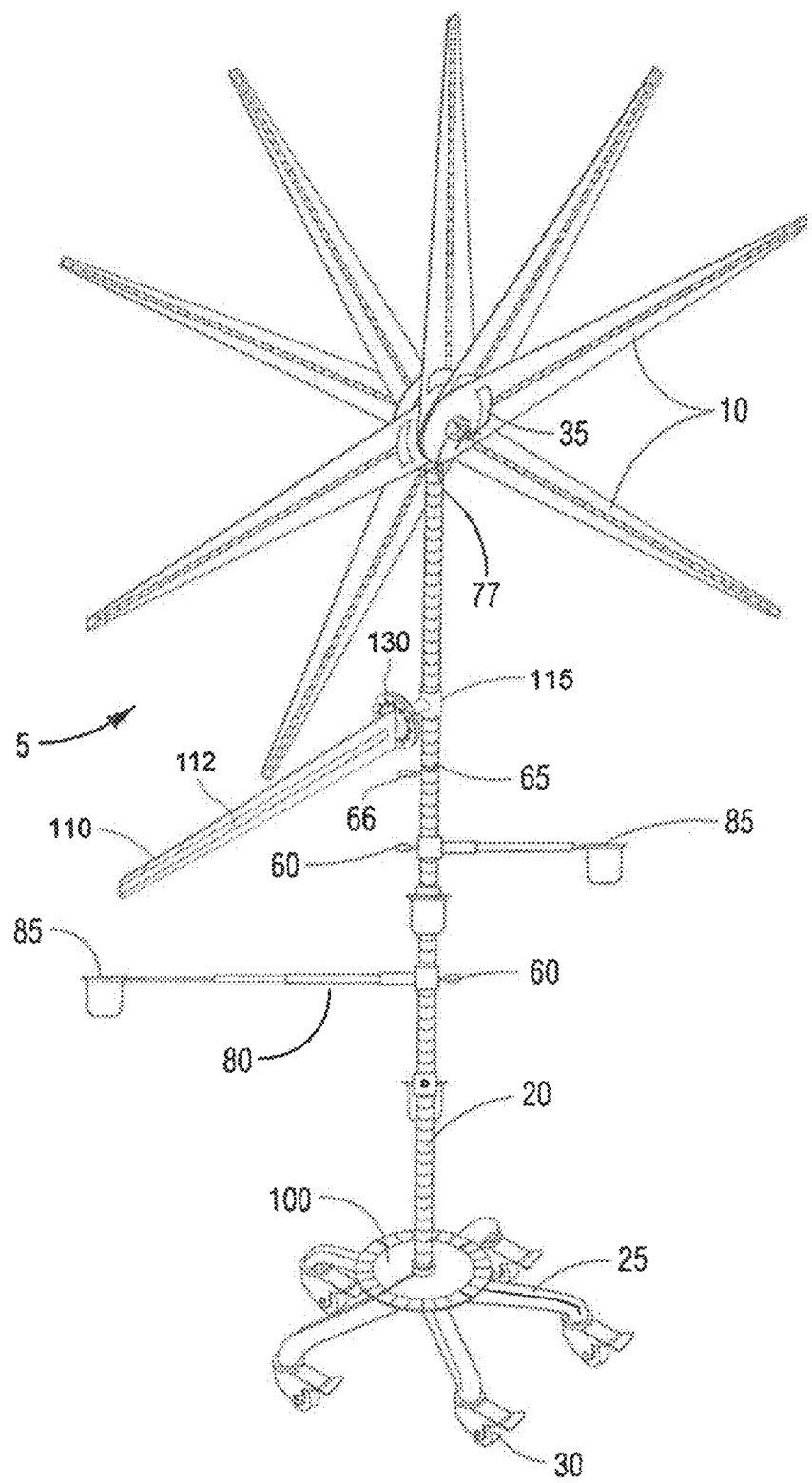
FIG. 1 is an isometric view of the device with the vertical arms and the horizontal arm depicted.
Figure 2:
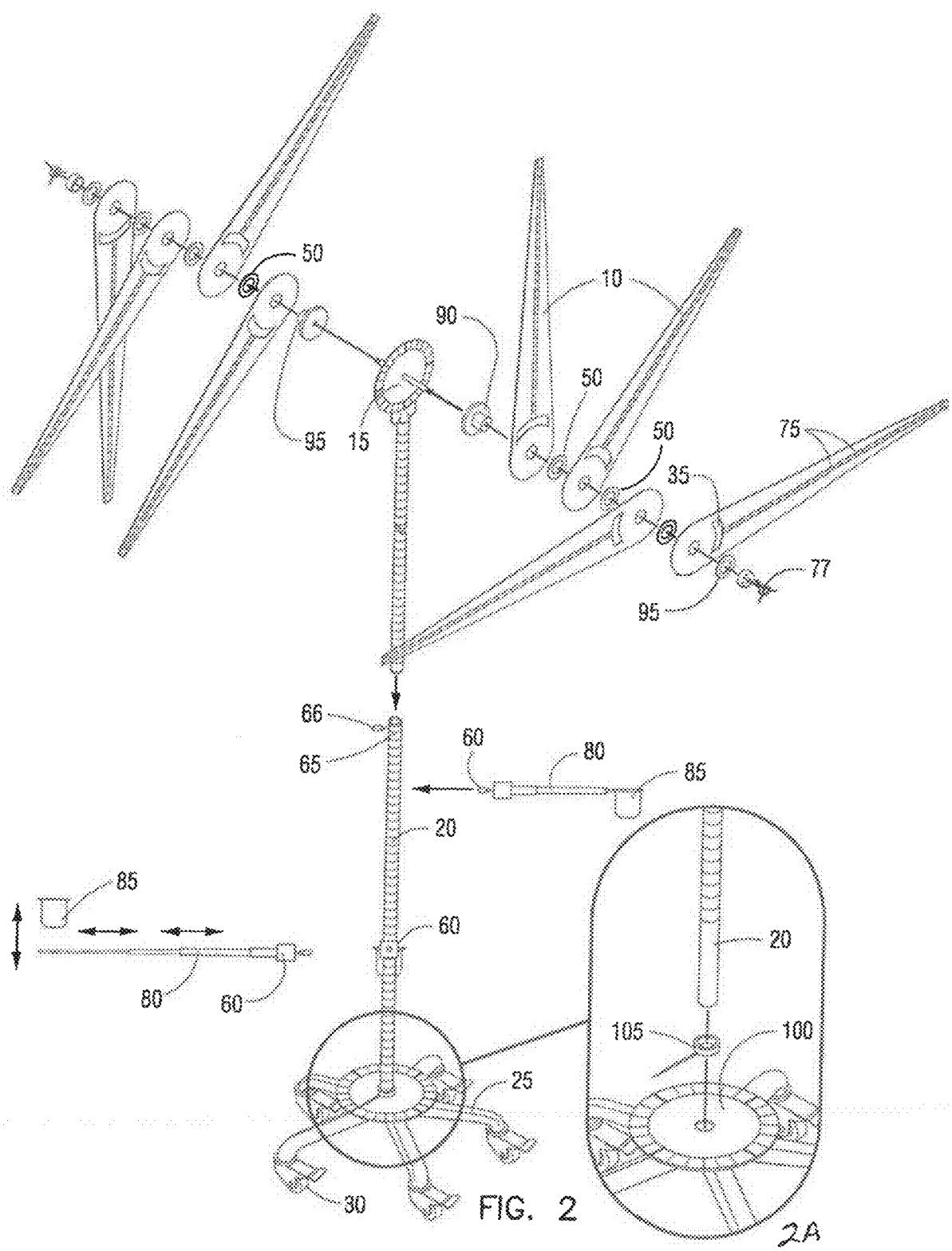
FIG. 2 is an exploded isometric view of the device with the retractable buckets and the vertical arms separated from the stand.
Figure 3:
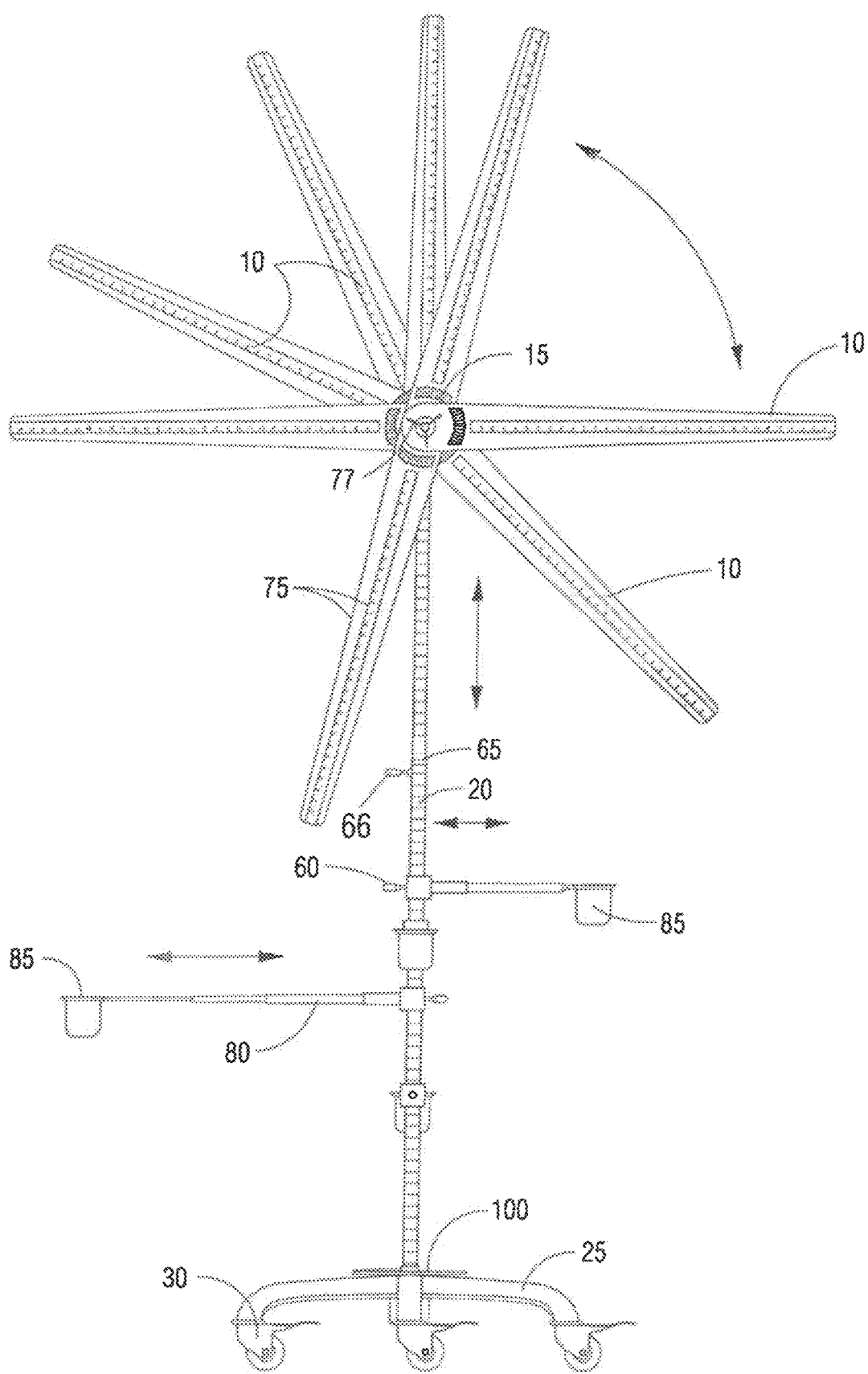
FIG. 3 is a front view of the device with the vertical arms and retractable buckets depicted but without the horizontal arm depicted.
Figure 4:
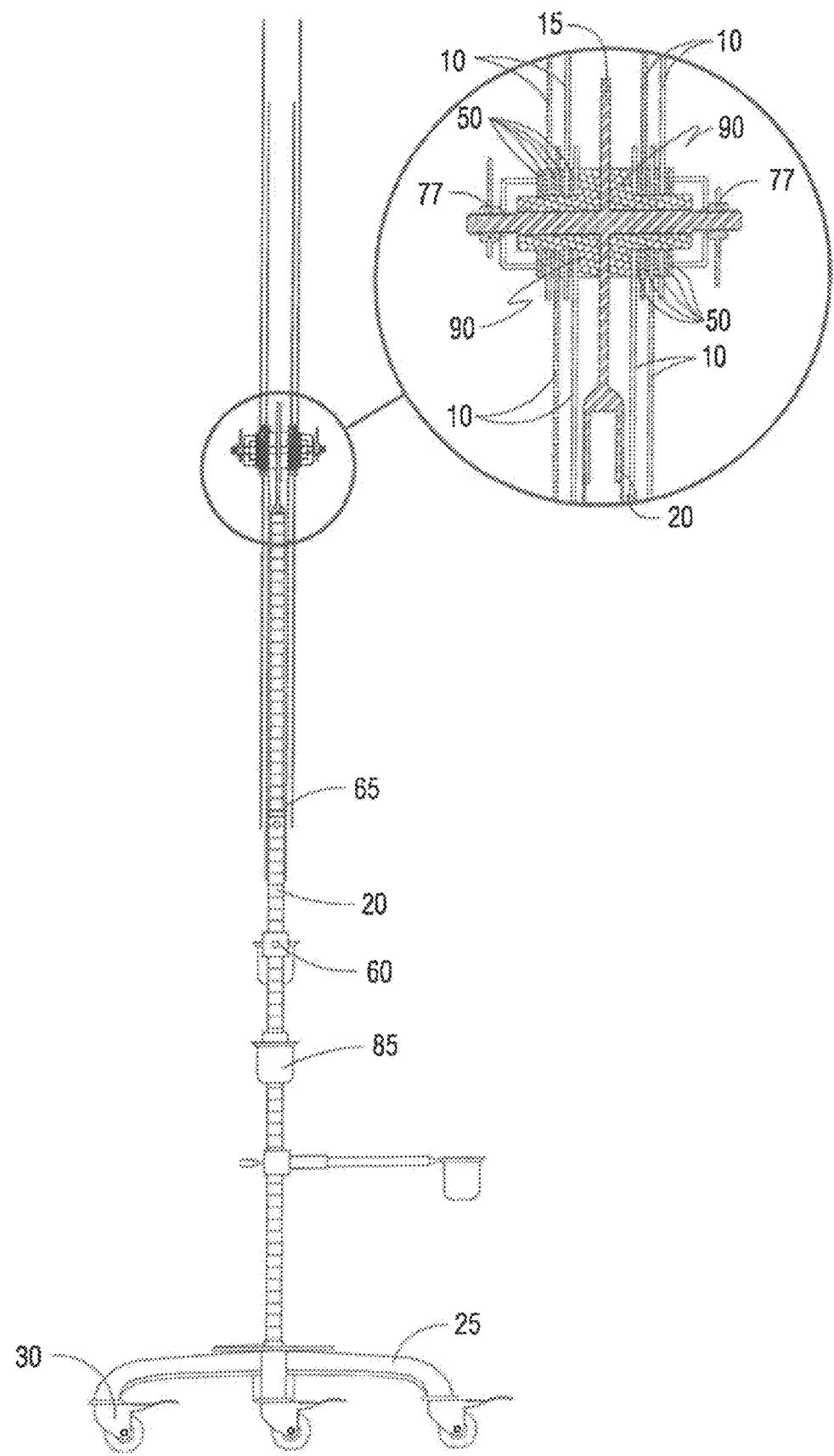
FIG. 4 is a side view of the device with an enlarged view of the connection means for the arms.
Figure 5:
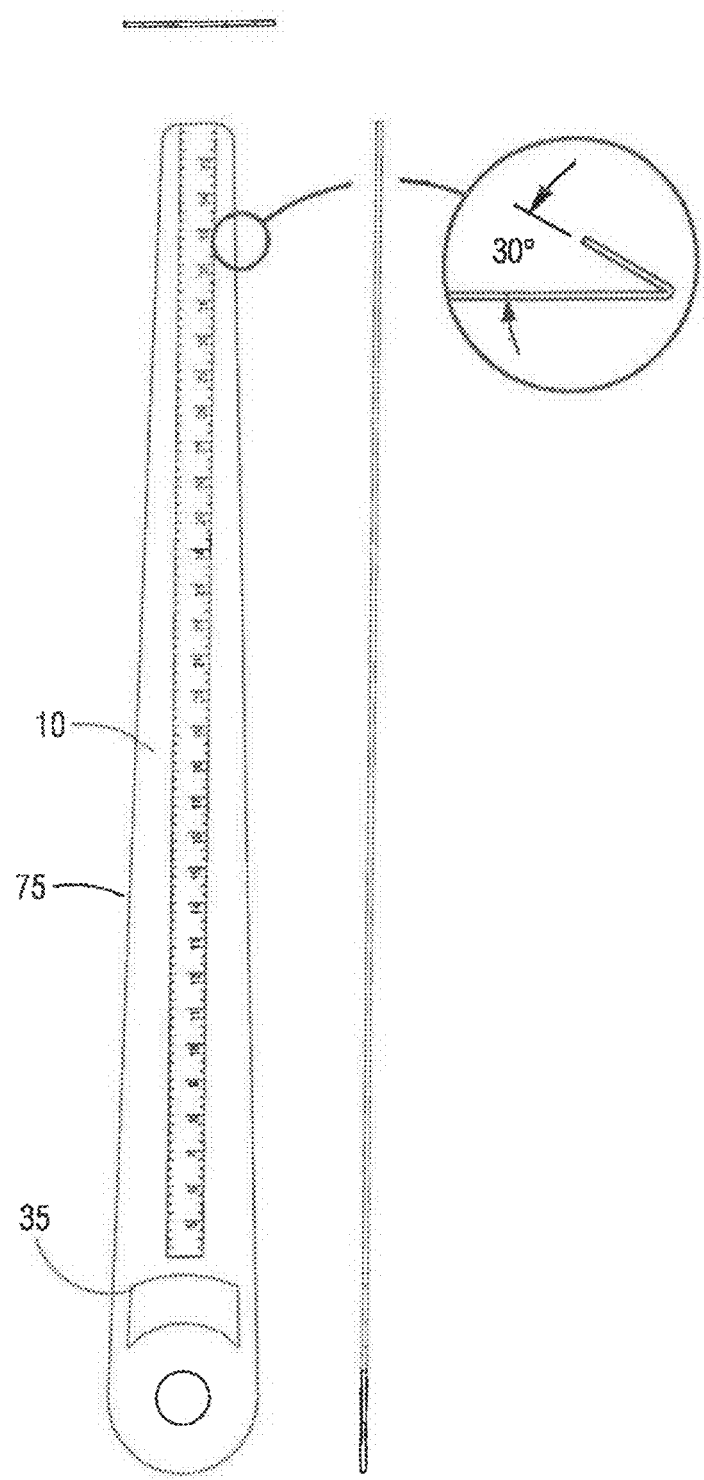
FIG. 5 is a front view of the vertical arm with the window depicted at the end of the arm.
Figure 6:
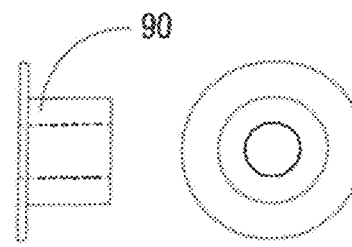
FIG. 6 is a side view of the bushing.
Figure 7:
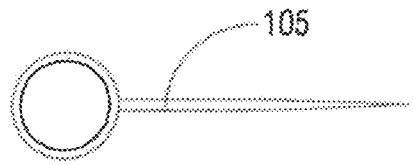
FIG. 7 is a top view of the protractor pointer.
Figure 8:
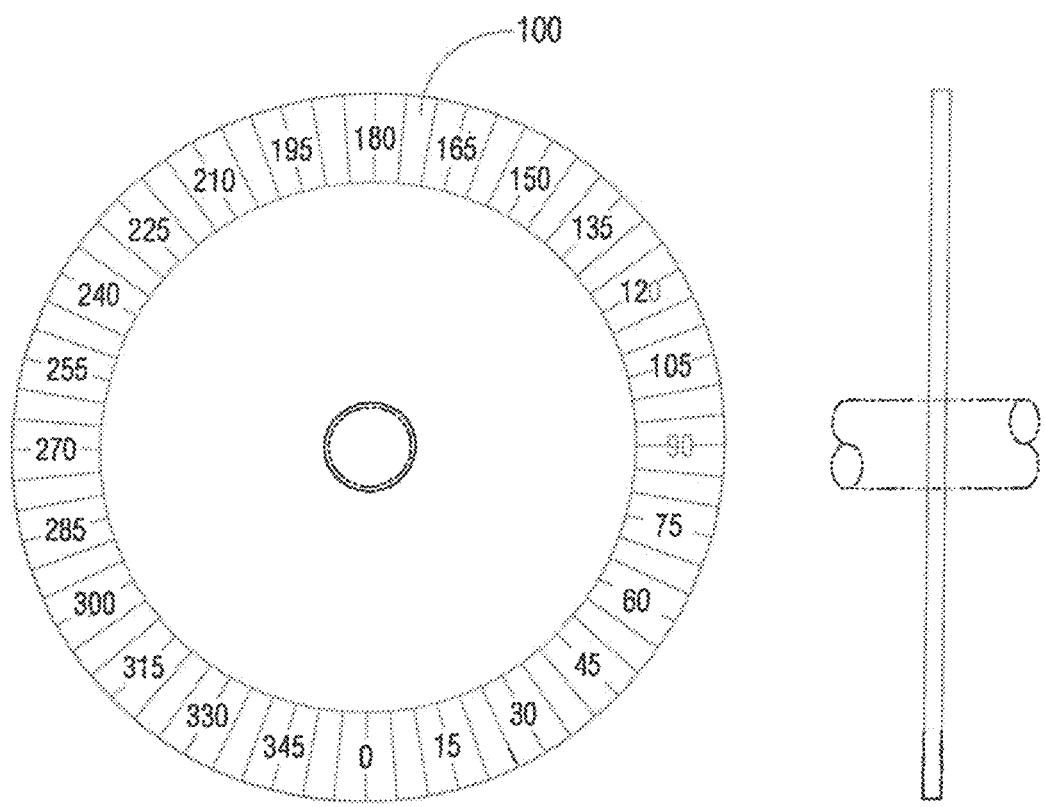
FIG. 8 is top view of the base protractor.
Figure 9:
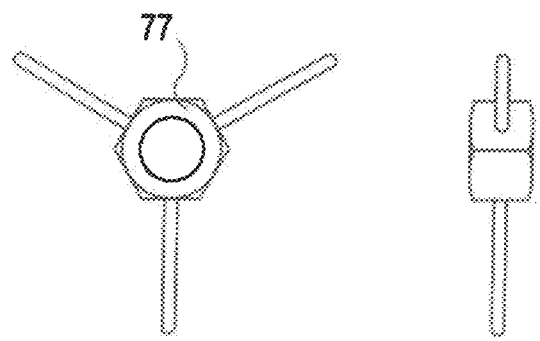
FIG. 9 is a front view of the tripod nut.
Figure 10:
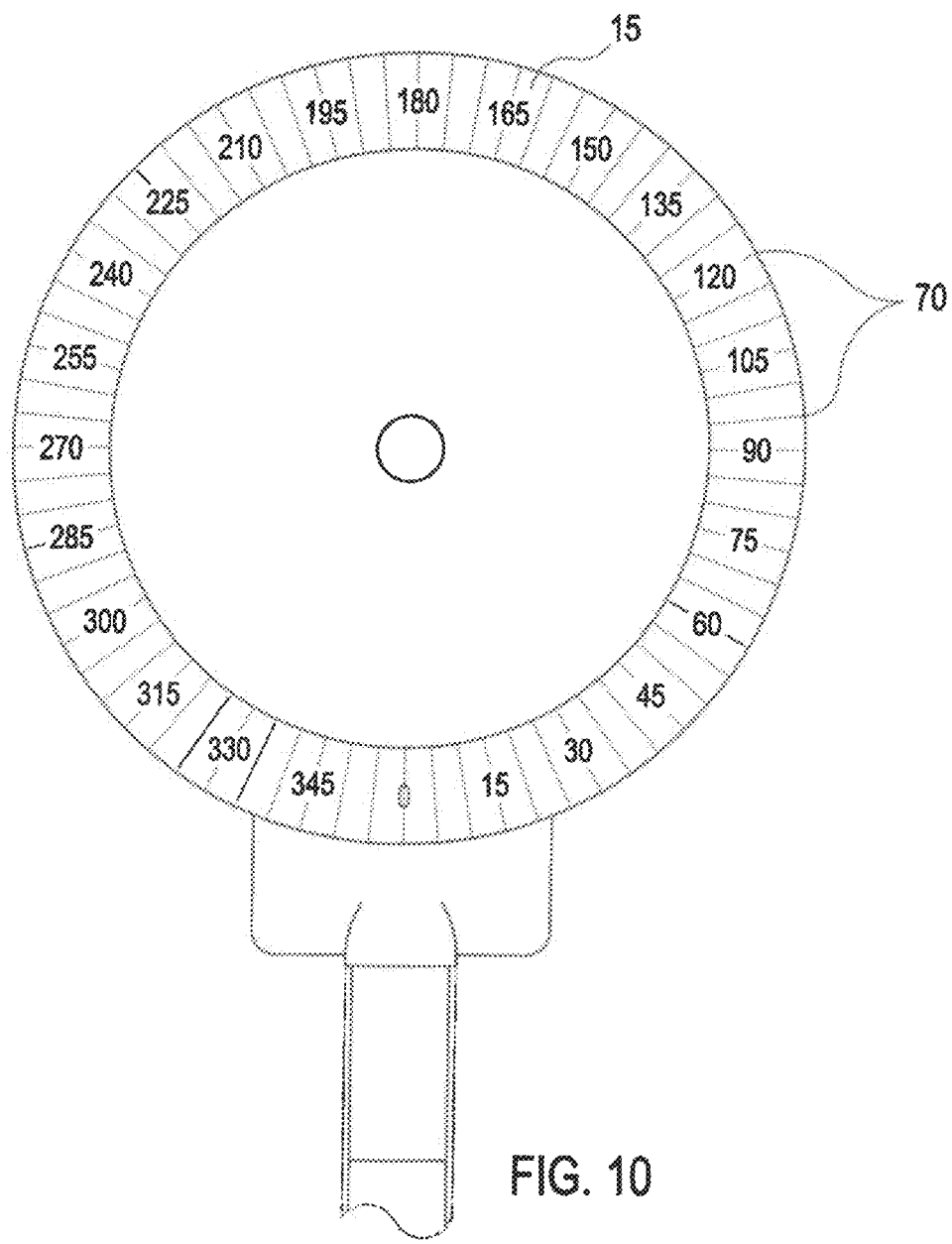
FIG. 10 is a front view of the protractor.
Figure 11:
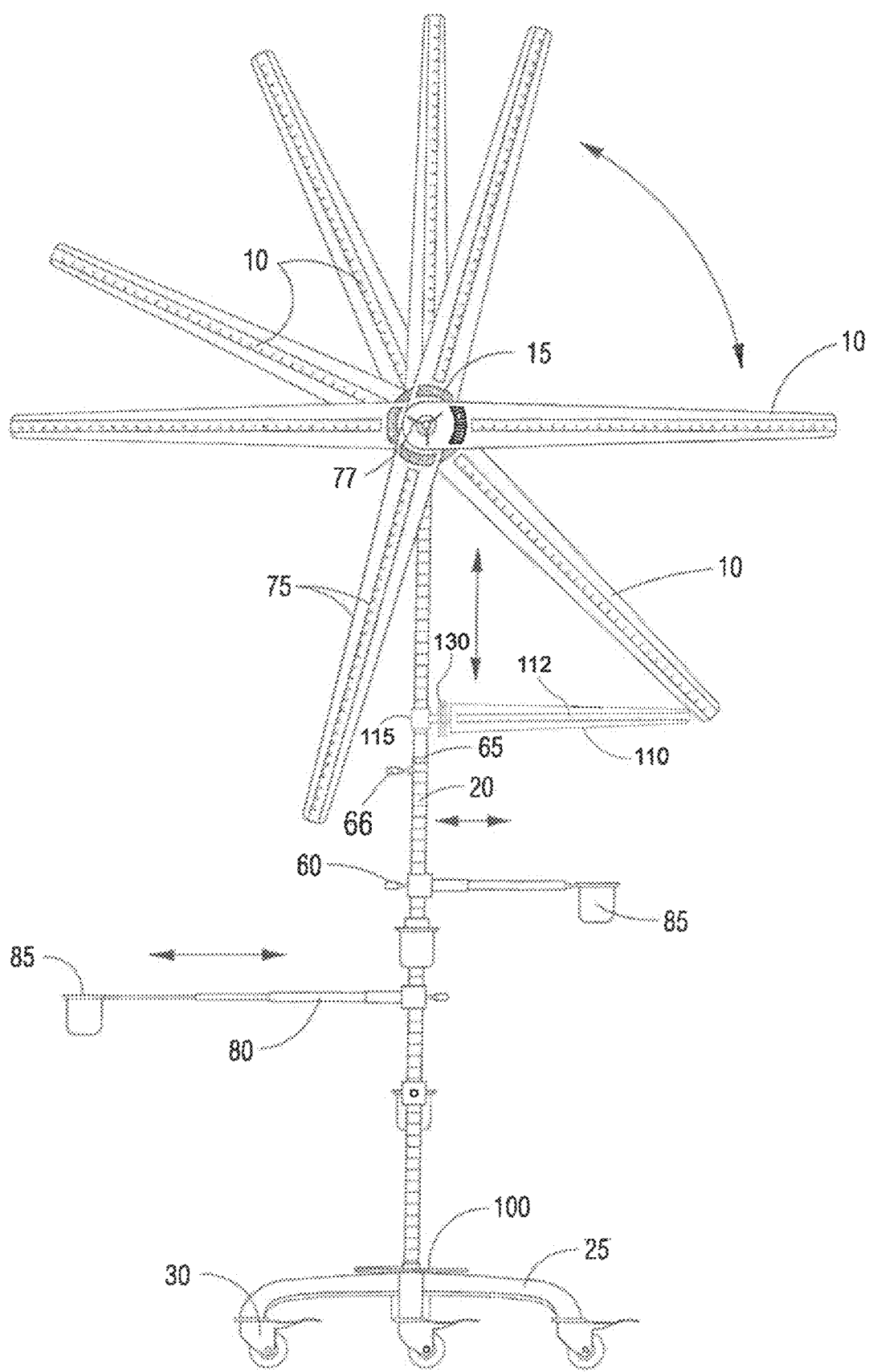
FIG. 11 is a front view of the device with the vertical arms and the horizontal arm and retractable buckets depicted.
Figure 12:
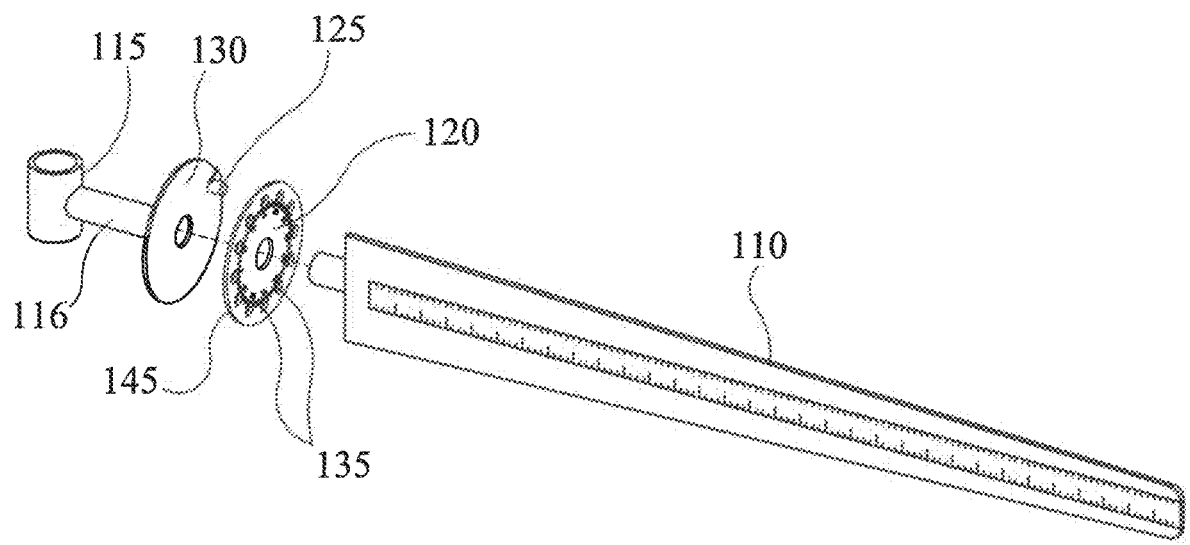
FIG. 12 is a perspective view of the horizontal arm depicting the attachment means with the flange and pin and grommet.

5—Device
10—Vertical Arms
15—Protractor
20—First pole
25—Base
30—Wheels
35—Window and arm
50—Washer
60—Attachment means for basket
65—Second pole
66—Locking Means for Stand
70—Degree markings on protractor
75—Gradient markings on arm
77—Tripod Nut
80—Basket Arm
85—Basket
90—First Bushing
95—Second Bushing
100—Base protractor
105—Base protractor pointer
110—Horizontal Arm
112—Gradations on the horizontal arm
115—Mounting device for Horizontal arm
116—Shaft
120—Horizontal arm protractor
125—Clasp with pin
130—Flange
135—Second Plate Openings
145—Second Plate for horizontal arm with openings

DETAILED DESCRIPTION OF THE EMBODIMENTS

This is a device that will enable the health care professional to accurately assess the neuromuscular functioning of a patient. It is designed to be portable and rests on a plurality of wheels.

The rehabilitation device 5 will rest on a base 25 and is comprised of a straight first pole 20 that is secured to the base 25. The base 25 will have wheels 30 that will be lockable so the device can be moved into a position and then be locked in place. The base will secure the first pole 20. A second pole 65 will be inserted into a portion of the first pole 20, which is partially hollow. The height of the first pole 20 can be adjusted so that the height of different individuals can be accommodated with this device; the two pole sections are connected together using a means of connection 66, which may be a set screw although other types of connection means may be used. Ideally the tripod nut 77 that secures the arms 10 will align with the person's sternum and appropriate alignment of the second pole section 65 is made by the therapist.

On the base 25 will be a plurality of attachment means 60 for baskets 85 to accommodate the different heights of individuals when testing for neuromuscular function from side to side or forward bend to reach below the waist.

A basket 85 that can telescope outward and away from the stand will be used to test the range of motion of a person bending forward and outward as well as sideways and backward below the waist. It is contemplated that there will be four baskets attached to the first pole section 20. Each of the baskets will be attached to telescoping arms 80 so that the therapist can adjust the length of the basket away from the stand 20.

On one first end of the second pole 65 will be a member that has an opening through which a pin (not depicted) will be inserted. On the pin will be two bushings 90,95 and washers 50 to secure the arms 10 and a protractor 15. It is contemplated that a specially designed tripod nut 77 will be used to secure the arms and protractor 15 in place. The tripod nut 77 can be moved easily be the therapist.

The protractor 15 that has three hundred and sixty degrees represented on it will be placed behind a plurality of arms 10.

It is contemplated that there will be eight arms 10 to cover the significant directions on a compass (north, northeast, east, southeast, south, southwest, west and northwest), and each arm 10 will be three to four feet in length for a total of six to eight feet across to insure that all heights of individuals or lengths of arms may be tested for the ability to reach in all directions away from the person.

On each of the vertical arms 10, markings 75 will be calibrated like a ruler so that the therapist can easily quantify the distance away from a central point that the person's reach in any given direction can be accurately measured.

A window 35 will appear on the proximal end of the vertical arm 10 so that the therapist can read the degrees on the protractor 15 that is located behind the arm 10 at a given angle position. There will be a plurality of degree marks on the protractor 15 so the therapist can easily quantify the degree at which the vertical arm 10 is positioned. The position of the vertical arms 10 as well as the length that the person can reach along a vertical arm enables the therapist to assess a person abilities and to measure the progress of the person's abilities.

The vertical arms 10 can be locked in place using the tripod nut 77 and all the arms are designed to work independently of each other. A first and second bushing 90, 95 secures the plurality of arms to one end of the second straight pole 65 on both sides of the second straight pole and permits rotation of the plurality of arms.

Because some persons may have vision or hearing problems there may be a means to illuminate the arms or emit an audible sound for the person who is being tested. Additionally, it may be easier for an individual to place objects on the arm so the use of magnetic objects to be placed on the metallic arms is also contemplated.

Additionally, the arms 10 will be color coded so that the health care professional can accurately test the proper movement of a person's eyes. For instance, the health care professional may ask the patient to move his or her eyes from the red arm to the green arm, after they have been placed in the appropriate position and observe the movement of the eyes. This type of movement will enable the therapist to evaluate the person's eye functions as well as the cognitive functions.

Around the protractor 15, there will be degree markings 70 on the protractor, which has three hundred and sixty degrees so the therapist can easily quantify the specific angle at which the vertical arm 10 is positioned. On each of the vertical arms will be a clear opening 35 at one end of the arm 10 to enable the therapist to read the degree of angle at which the arm is positioned.

A horizontal arm 110 with gradations is mounted to the pole 20 at a height selected by the therapist; the horizontal arm can be moved up and down on the pole. The horizontal arm 110 allows the therapist to judge the ability of the person to move his or her arms, hands and wrist in front of the person and to the side of the person.

The horizontal arm 110 is mounted on the second pole 65 such as depicted in FIG. 1 using the mounting device for the horizontal arm 115. The horizontal arm 110 can be moved up or down the second pole 65 to accommodate for the height of a particular patient. A means to lock (not depicted) the horizontal arm in place is also provided.

Figure 13A:
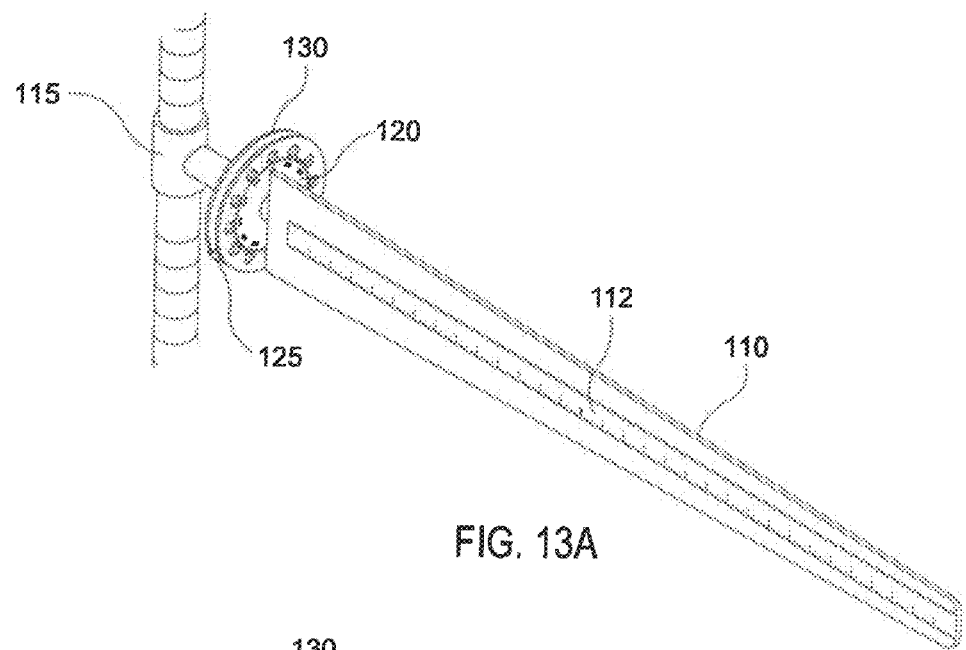
FIG. 13A is a partial perspective view of the horizontal arm attached and the horizontal arm placed in a vertical position.
Figure 13B:
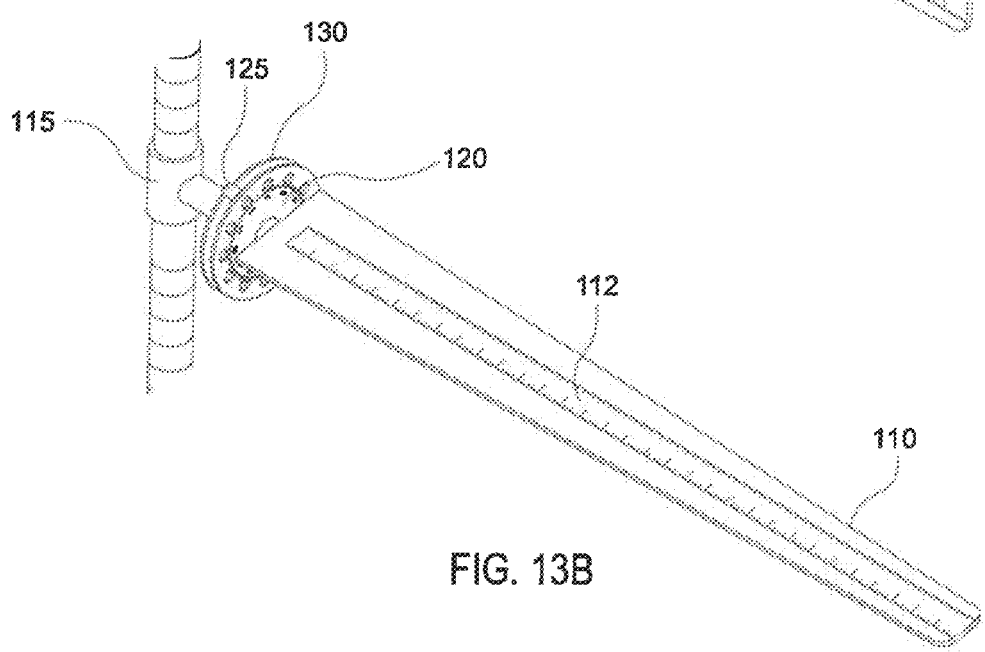
FIG. 13B is a partial perspective view of the horizontal arm and the horizontal arm placed in a horizontal position.

On the mounting device 115 will be positioned a flange 130 for the horizontal arm 110 with a clasp and pin 125 on the flange 130. The shaft from the mounting device 116 is inserted through the opening of a second plate for the horizontal arm 145; the second plate for the horizontal arm 145 has a plurality of openings 135 into which the pin portion of the clasp with pin 125 is inserted to lock the horizontal arm 110 in position. After the pin is inserted into an opening 135 the horizontal arm 110 can be locked into position. The openings 135 on the second plate 145 allow the therapist to rotate the horizontal arm 110 to a desired position such as depicted in FIGS. 13A and 13B.

The horizontal arm 110 has a first end and a second end. The horizontal arm 110 at the first end is inserted through the opening of the second plate 145 and into the opening of the flange 130; the mounting device 115 is inserted into the opening of the hollow portion of the horizontal arm. A second plate 145 at the first end of the horizontal arm 110 is positioned with a plurality of openings. A clasp and pin assembly that is positioned on the flange of the mounting device allows the horizontal arm to be rotated along a horizontal axis to lock the horizontal arm in place. The ability to rotate the horizontal arm allows the therapist to assess the person's ability to use his or her wrist in different positions.

Gradations 112 are placed on the horizontal arm to enable the medical personnel to objectively measure the ability of the person to extend his or her arm in front and to the side.

A horizontal arm protractor 120 is placed on the plate for the horizontal arm. A plurality of openings is placed on the first end of the horizontal arm to allow the therapist to lock the horizontal arm in position using a pin that is inserted through the plurality of openings. This allows the therapist to obtain objective measurements regarding the person's ability to rotate the wrist and/or hand.

The purpose of the device is for a therapist to measure the physical progress for a patient who is suffering from neuromuscular dysfunction and can easily and objectively quantify the degree of improvement and highlight areas of improvement that may be needed. The data that can be measured is done in such a way so that the data can easily be read from therapist to therapist as the patient continues with his or her recovery.

During use the therapist would place the device in a given position and arrange the position of the arms according to the prescribed area of neuromuscular functioning to be tested. This may involve the position of the vertical arms or horizontal arm as well as the position of the baskets.

The patient is placed in front of the device and the tripod nut 77 is positioned at about the level of the sternum of the person when the person is facing the device or at the acroniom process of the patient if the patient is positioned sideways with respect to the device. The therapist then instructs the patient to move in certain directions such as reaching in certain directions. As the person moves in a direction the person may touch one of the arms and the measurements are recorded. The therapist customizes the commands to the patient depending on the specific issue(s) to be addressed by the therapist and suggested therapy.

A base protractor 100 will be affixed to the top of a base plate. On the top surface of the base protractor 100 will be a base protractor pointer 105 that can rotate over the top surface of the base protractor 100. The therapist can place the base protractor pointer 105 on a designated angle relative to the person and move the device so that the person's ability to reach at an angle can be objectively measured. This type of movement is critical to determine whether the person can reach to place items in a cabinet or in a refrigerator, typically by reaching at an angle as well reaching directly in front of the person. With the base protractor pointer, the therapist can move the device to a multitude of positions relative to the patient and measure the displacement with respect to the patient.

As the patient is performing the different physical activities, the therapist is recording the physical measurements according to the gradations on the vertical arms and the angle that is read on the protractor for or during exercises. The patient may similarly be asked to perform physical maneuvers such as placing items in or out of the basket(s) that have been extended away from the stand. Similarly, the therapist records the distance away from the stand that the person can place and/or retrieve objects.

Ideally the therapist charts the data so that the next therapist who interacts with the patient can determine quickly the progress that a patient has made.

When not in use, the vertical arms 10 can be locked and stored in vertical alignment.

While the embodiments of the invention have been disclosed, certain modifications may be made by those skilled in the art to modify the invention without departing from the spirit of the invention.

The invention claimed is:

1. A neuromuscular testing device which is comprised of:
    a. a base;
        wherein the base is of a predetermined size;
        wherein a plurality of wheels are placed on a bottom of the base; and
        wherein a base pate is placed on the base;
    b. a first pole;
        wherein the first pole is secured to the base;
        wherein the first pole can be locked in place;
        said first pole can telescope; and
        wherein one end of the first pole is hollow;
    c. a base protractor;
        wherein the base protractor is affixed to the base; and
        said base protractor has markings for three hundred and sixty degrees;
    d. a base protractor pointer;
        wherein the base protractor pointer is free to rotate over a top surface of the base protractor;
    e. a second pole;
        wherein a portion of the second pole is inserted into the one end of the first pole;
        wherein a means of connection is provided to secure the first pole to the second pole;
        wherein a protractor is attached to a first end of the second pole;
        said protractor has markings for three hundred and sixty degrees;
        wherein an opening is provided on the first end of the second pole;
        wherein a pin passes through the center of the opening;
        said pin supports a plurality of bushings; and
        said pin supports a plurality of washers;
    f. a plurality of vertical arms;
        wherein each vertical arm of the plurality of vertical arms is of a predetermined length;
        wherein a series of markings are placed on each vertical arm of the plurality of vertical arms;
        said markings indicate a distance from the first opening on the first end;
        wherein the plurality of vertical arms operate independently of each other; and
        wherein the plurality of vertical arms is color coded;
    g. a window provided on one end of each vertical arm of the plurality of vertical arms;
        wherein each window is placed over the protractor; and
        each window permits a therapist to record measurements;
    h. a plurality of baskets;
        wherein each basket of the plurality of baskets is attached to the second pole;
        each basket of the plurality of baskets extends horizontally away from the second pole; and
        each basket of the plurality of baskets can be removed from the second pole;
    i. a means to lock the plurality of vertical arms;
    j. a horizontal arm;
        wherein the horizontal arm is a predetermined length;
        wherein the horizontal arm is attached to the second pole;
        wherein the horizontal arm has a first end and a second end;
        wherein the first end of the horizontal arm is hollow;
        wherein gradations are provided on the horizontal arm; and
        wherein the horizontal arm can rotate along a horizontal axis;
    k. a mounting device for the horizontal arm;
        wherein a shaft extends from the mounting device;
        wherein a flange is placed at an end of the shaft extending from the mounting device; and
        wherein a clasp and pin are attached to the flange on the end of the shaft; and
    l. a second plate for the horizontal arm;
        wherein the second plate for the horizontal arm has a plurality of openings;
        wherein a horizontal arm protractor is provided on the second plate for the horizontal arm.

2. The device as described in claim 1 wherein a magnetic item is placed on each vertical arm of the plurality of vertical arms.

3. The device as described in claim 1 wherein the means to lock the plurality of vertical arms is a tripod nut.

4. A method to use the device as described in claim 1 which is comprised of the following steps:
    a. placing the device at a given position;
    b. positioning the plurality of vertical arms of the device in a predetermined configuration;
    c. positioning the horizontal arm of the device in a predetermined configuration;
    d. positioning the baskets of the device in a predetermined configuration;
    e. placing the device at an angle relative to a patient;
    f. asking the patient to perform certain physical activities including functional reaching in multiple directions and planes and extending the patient's arms below their waist; and
    g. recording measurements from the stand relative to the patient while the patient performs the certain physical activities using the base protractor and the plurality of vertical arms of the device.

* * * * *